(12) United States Patent
Murray et al.

(10) Patent No.: US 10,485,668 B2
(45) Date of Patent: Nov. 26, 2019

(54) KNEE PROSTHESIS

(71) Applicants: David Wycliffe Murray, Oxford (GB); Paul Monk, Oxford (GB)

(72) Inventors: David Wycliffe Murray, Oxford (GB); Paul Monk, Oxford (GB)

(*) Notice: Subject to any disclaimer, the term of this patent is extended or adjusted under 35 U.S.C. 154(b) by 0 days.

(21) Appl. No.: 15/556,062

(22) PCT Filed: Mar. 7, 2016

(86) PCT No.: PCT/GB2016/050605
§ 371 (c)(1),
(2) Date: Sep. 6, 2017

(87) PCT Pub. No.: WO2016/142676
PCT Pub. Date: Sep. 15, 2016

(65) Prior Publication Data
US 2018/0055647 A1    Mar. 1, 2018

(30) Foreign Application Priority Data
Mar. 6, 2015   (GB) .................................. 1503838.3

(51) Int. Cl.
*A61F 2/38*   (2006.01)
*A61B 17/15*  (2006.01)
*A61F 2/64*   (2006.01)
*A61F 2/68*   (2006.01)

(52) U.S. Cl.
CPC ............ *A61F 2/3877* (2013.01); *A61F 2/38* (2013.01); *A61F 2/389* (2013.01); *A61F 2/3859* (2013.01); *A61F 2/3868* (2013.01); *A61F 2/3886* (2013.01); *A61B 17/155* (2013.01); *A61F 2/64* (2013.01); *A61F 2/68* (2013.01); *A61F 2002/3881* (2013.01)

(58) Field of Classification Search
CPC ............ A61F 2/3877; A61F 2002/3881; A61F 2002/648
USPC ............................................... 623/20.18–20.2
See application file for complete search history.

(56) References Cited

U.S. PATENT DOCUMENTS

| 6,102,955 | A | * | 8/2000 | Mendes | A61B 17/1637 |
| | | | | | 623/20.32 |
| 2012/0310362 | A1 | * | 12/2012 | Li | A61F 2/38 |
| | | | | | 623/20.32 |
| 2014/0142713 | A1 | * | 5/2014 | Wright | A61F 2/3859 |
| | | | | | 623/20.21 |

FOREIGN PATENT DOCUMENTS

| DE | 100 62 715 A1 | * | 11/2002 | ............... | A61F 2/38 |
| JP | 2002-035020 A | * | 2/2002 | ............... | A61F 2/38 |

* cited by examiner

*Primary Examiner* — David H Willse
(74) *Attorney, Agent, or Firm* — Michael T. Abramson; Holland & Knight LLP

(57) ABSTRACT

A femoral component (101) for a knee prosthesis, the femoral component (101) comprising: a body portion (103) having: a lateral portion (109) and a medial portion (111) when in an implanted configuration, wherein a parasagittal plane is located at the intersection between the lateral portion (109) and the medial portion (111); and a patella track (105) extending anterior-posteriorly around the body portion (103), wherein the patella track (105) comprises a first patella track portion (105a) that is directed laterally away from the parasagittal plane as it extends towards a posterior end of the patella track (105).

17 Claims, 4 Drawing Sheets

KNEE PROSTHESIS

CROSS-REFERENCE TO RELATED APPLICATIONS

This application is a U.S. National Stage of International Patent Application No. PCT/GB2016/050605, filed 7 Mar. 2016, which claims priority to Great Britain Patent Application No: 1503838.3, filed on 6 Mar. 2015, the disclosure of which is incorporated herein by reference in its entirety.

This disclosure relates to components for a knee prosthesis, and in particular, but not exclusively, relates to a femoral knee prosthesis having a patella track configured to guide a natural patella or a prosthetic patella during flexion of the knee.

INTRODUCTION

Knee replacement typically involves resecting the femur and tibia bones and implanting femoral and tibial prosthetic components. The procedure may be a total knee replacement, in which all articulating surfaces of the knee joint are replaced, or a partial knee replacement in which only some of the articulating surfaces of the knee joint are replaced, such as a bi-compartmental or unicondylar knee replacement.

In many total knee replacements, a femoral component is configured to engage and articulate with a bearing component that is supported by a tibial component. In some total knee replacement procedures the natural patella is replaced with a prosthetic patella component. The femoral component is configured to engage and articulate with the natural patella (or the prosthetic patella) as the knee joint moves through its range of motion.

Problems that occur following knee arthroplasty may relate to the patello-femoral joint and may be caused by abnormal patella tracking. Patello-femoral kinematics are therefore an important consideration in the design of the femoral component, the tibial component and the prosthetic patella of a knee prosthesis.

With traditional designs of total knee replacements, the femoral component is symmetrical with the trochlear groove (patella track) running straight down the centre of the femoral component between the medial and lateral condyles. In more modern designs of total knee replacements the femoral component and the patella track are asymmetric. An example of such a component is shown in FIG. 5. In such an implant the patella track (indicated generally by line 501) is directed medially from an anterior/proximal location at the start of the track towards a centre line 503 of the implant. The track then runs generally parallel along the centre line 503 between the condyles of the implant.

This design results in the patella moving generally medially with increasing knee flexion, until it articulates with the condyles, after which the patella will then continue generally straight. This patella motion is unnatural, and can lead to the patella-femoral joint problems discussed above.

It is desirable to design the femoral component so as to improve patella tracking during articulation of the knee joint.

STATEMENTS OF INVENTION

According to an aspect of the present disclosure there is provided a femoral component for a knee prosthesis. The femoral component comprises a body portion. The body portion comprises a lateral portion and a medial portion when in an implanted configuration. A patella track extends anterior-posteriorly around the body portion, and a first patella track portion is directed laterally as it extends towards a posterior end of the patella track. "Extends" as used in the sentence above refers to the progression of the patella track around the component, rather than to the extension of the knee: the track is directed laterally as it progresses towards the posterior end of the component. Thus, when the femoral component is in use in a knee joint, the patella track is shaped to guide a patella laterally during flexion of the joint. This advantageously mimics the motion of the patella in a natural knee joint.

A parasagittal plane may be located at an intersection between the lateral portion and the medial portion. The parasagittal plane may be coincident with the centreline of the femoral component, for example when the component is for use in a total knee replacement or patello-femoral replacement. Alternatively, a parasagittal plane may be located at or near a medial edge of the femoral component, for example if the component is for use in a lateral unicondylar knee replacement. The first patella track portion may be directed laterally relative to (e.g. away from) the parasagittal plane as it extends towards a posterior end of the patella track.

The first patella track portion may start at a point on the parasagittal plane. The first patella track portion may start at a point laterally or medially of the parasagittal plane. The first patella track portion may diverge progressively further laterally from its starting point at or near the parasagittal plane as it extends towards the posterior end of the patella track. The first patella track portion may be configured to guide the motion of a natural patella or a prosthetic patella during articular motion of the knee. As the knee articulates from a position where the knee is partially flexed towards a position where the knee is fully flexed, the natural patella or the prosthetic patella may track laterally away from the parasagittal plane. In this manner, patello-femoral kinematics may be improved during flexion of the knee.

The patella track may comprise a second patella track portion that is directed laterally away from the parasagittal plane as it extends towards an anterior/proximal end of the patella track. The second patella track portion may start at a point on the parasagittal plane. The second patella track portion may start at a point laterally or medially of the parasagittal plane. The second patella track portion may diverge progressively further laterally from its starting point at or near the parasagittal plane as it extends towards the anterior/proximal end of the patella track.

The first patella track portion and the second patella track portion may extend continuously into each other. The first patella track portion and the second patella track portion may be joined by one or more connecting portions of the patella track. For example, the patella track may comprise a third patella track portion configured to join the first patella track portion to the second patella track portion.

The third patella track portion may run along the parasagittal plane, or adjacent to the parasagittal plane. The third patella track may be curved.

The second patella track portion may be configured to guide the motion of a natural patella or a prosthetic patella during articular motion of the knee. As the knee articulates from a position where the knee is partially flexed towards a position where the knee is fully extended, the natural patella or the prosthetic patella may track laterally away from its starting point at or near the parasagittal plane. The patella track may comprise a groove having a depth, and the depth of the groove may be shallower (i.e. the component may be flatter) at the anterior/proximal end of the second patella track portion than it is at a posterior end of the second patella track portion. The groove may additionally or alternatively be wider at the anterior end.

In a femoral component for use in a total knee replacement, the lateral portion of the body portion may comprise a medial edge portion. The medial portion of the body portion may comprise a lateral edge portion. The medial edge portion of the lateral portion and the lateral edge portion of the medial portion may at least partially form the lateral and medial edge portions of the patella track respectively.

In a femoral component for use in a unicondylar knee replacement, the component may be for use in lateral condyle, and a medial edge of the component may form part of the patella track. Alternatively, the component may be for use in a medial condyle, and a lateral edge of the component may form part of the patella track.

The patella track may comprise one or more articular surfaces configured to engage the natural patella or the prosthetic patella. The prosthetic patella may be at least partially anatomically shaped. The one or more articular surfaces of the patella track may be configured to at least partially conform to an articular surface of the natural patella or the prosthetic patella. The one or more articular surfaces of the patella track may be configured to engage a bearing component of the knee prosthesis.

The femoral component may comprise a bearing articular surface configured to engage a bearing component (e.g. of a prosthesis or the natural knee). A portion of the articular surface of the patella track may overlap with the bearing articular surface. A cross-section of the posterior end of the patella track may be substantially the same as a cross-section of the bearing articular surface such that the articular surface of the patella track blends smoothly into the bearing articular surface. The bearing articular surface may have a substantially constant cross-section.

The lateral portion may comprise a lateral condyle. The medial portion may comprise a medial condyle.

According to another aspect of the present disclosure there is provided a femoral component for a knee prosthesis. The femoral component comprises a body portion having a lateral portion and a medial portion when in an implanted configuration. A parasagittal plane is located at the midpoint between the lateral and the medial portions. The body portion comprises a patella track configured to guide a natural patella or a prosthetic patella laterally away from the parasagittal plane as the knee flexes, for example as the knee articulates from a position where the knee is partially flexed towards a position where the knee is fully flexed.

The patella track may comprise a first patella track portion extending away from the parasagittal plane towards a posterior side of the body portion. The first patella track portion may extend in an anterior-posterior direction and a medial-lateral direction.

The patella track may comprise a second patella track portion extending away from the parasagittal plane towards an anterior side of the body portion. The second patella track portion may extend in an anterior-posterior direction and a medial-lateral direction.

According to a further aspect of the present disclosure there is provided femoral component for a knee prosthesis. The femoral component comprises a medial condyle portion and a lateral condyle portion. The medial condyle portion and the lateral condyle portion each comprise an articular surface configured to engage a bearing component. The medial condyle portion and the lateral condyle portion are at least partially connected by a patella track portion. The patella track portion extends anterior-posteriorly around the femoral component. The patella track is at least partially disposed in between the medial condyle portion and the lateral condyle portion. The patella track portion is configured to engage a natural patella or a prosthetic patella. The patella track portion is configured to guide the motion of the natural patella or a prosthetic patella during articular motion of the knee. As the knee articulates from a position where the knee is partially flexed towards a position where the knee is fully flexed the natural patella or a prosthetic patella may track laterally away from a parasagittal plane located in between the medial and the lateral condyle portions.

According to a further aspect of the invention there is provided a tibial component comprising a lateral condyle having a lateral bearing surface configured to engage in use with a lateral condyle of a femoral component and a medial condyle having a medial bearing surface configured to engage in use with a medial condyle of a femoral component, wherein the lateral bearing surface is raised with respect to the medial bearing surface. The lateral bearing surface may be arranged to be, for example, 2-3 mm higher than the medial bearing surface when the component is implanted.

A parasagittal plane may be located between the lateral bearing surface and the medial bearing surface. The parasagittal plane may be coincident with the centreline of the tibial component. The tibial component may comprise coronal cross-section (i.e. a cross-section in the coronal plane) which is asymmetric about the parasagittal plane.

According to a further aspect of the invention there is provided a tibial component comprising a lateral condyle having a lateral bearing surface configured to engage in use with a lateral condyle of a femoral component and a medial condyle having a medial bearing surface configured to engage in use with a medial condyle of a femoral component, wherein the tibial component comprises a coronal cross-section which is asymmetric about a parasagittal plane coincident with a centre line of the component.

According to a further aspect of the invention, a kit for a knee prosthesis is provided, wherein the kit comprises a femoral component as described herein, and/or a tibial component as described herein, and a patella button.

The bearing surface of the tibial component may be shaped for use with a femoral component of the type described herein. The bearing surface of the tibial component may have a complementary shape to the distal articular surface of the femoral component in the coronal plane (i.e. when the femur is in extension) or the posterior articular surface of the femoral component when in flexion.

The patella button may be anatomically shaped. The articular surface of the patella track of the femoral component may be shaped to correspond to an articular surface of the patella button.

To avoid unnecessary duplication of effort and repetition of text in the specification, certain features are described in relation to only one or several aspects or embodiments of the invention. However, it is to be understood that, where it is technically possible, features described in relation to any aspect or embodiment of the invention may also be used with any other aspect or embodiment of the invention.

BRIEF DESCRIPTION OF THE DRAWINGS

For a better understanding of the present disclosure, and to show more clearly how it may be carried into effect, reference will now be made, by way of example, to the accompanying drawings, in which.

DETAILED DESCRIPTION

Figure 1A:
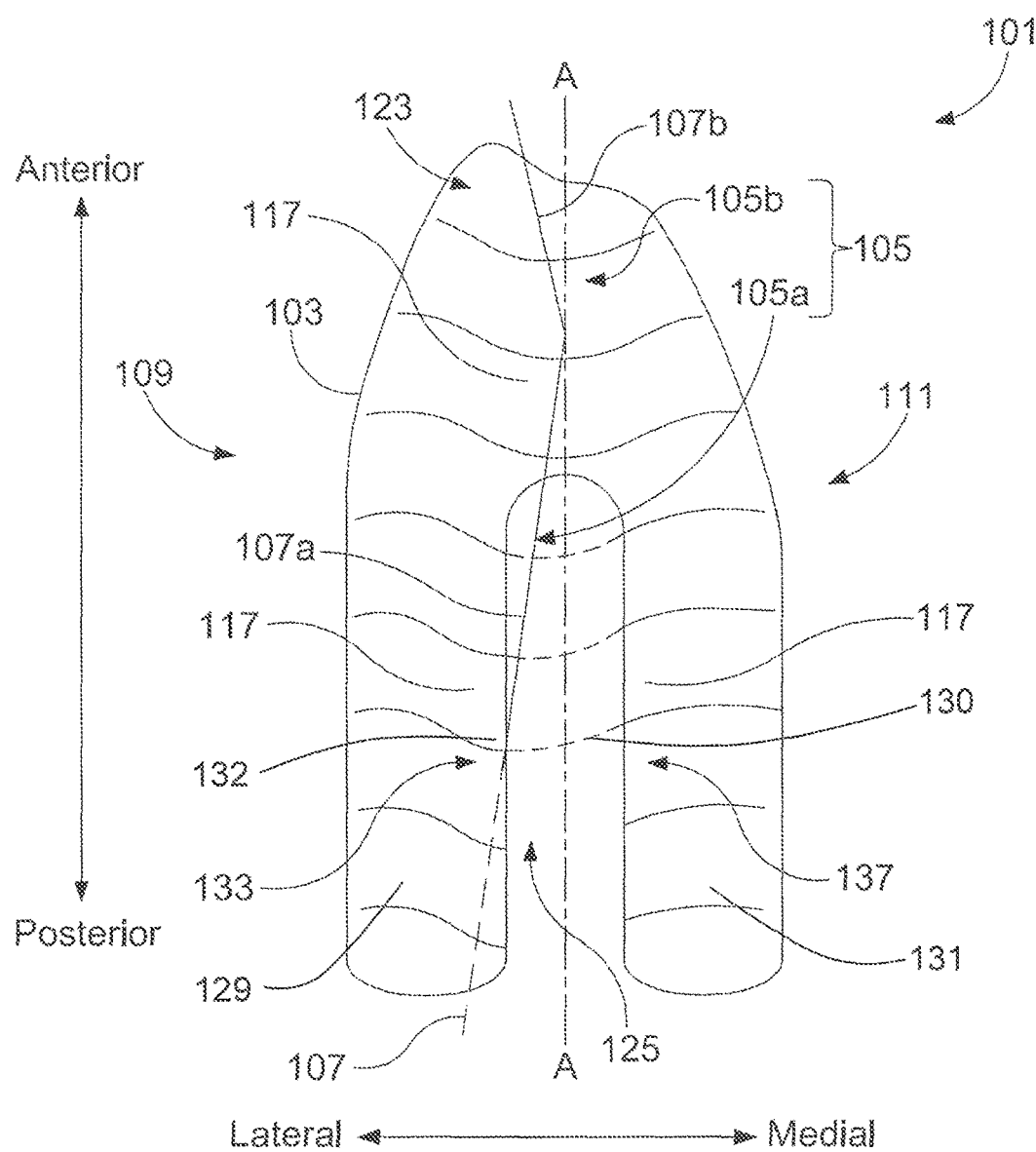
FIG. 1a shows a surface projection of a femoral component for a knee prosthesis.
Figure 2A:
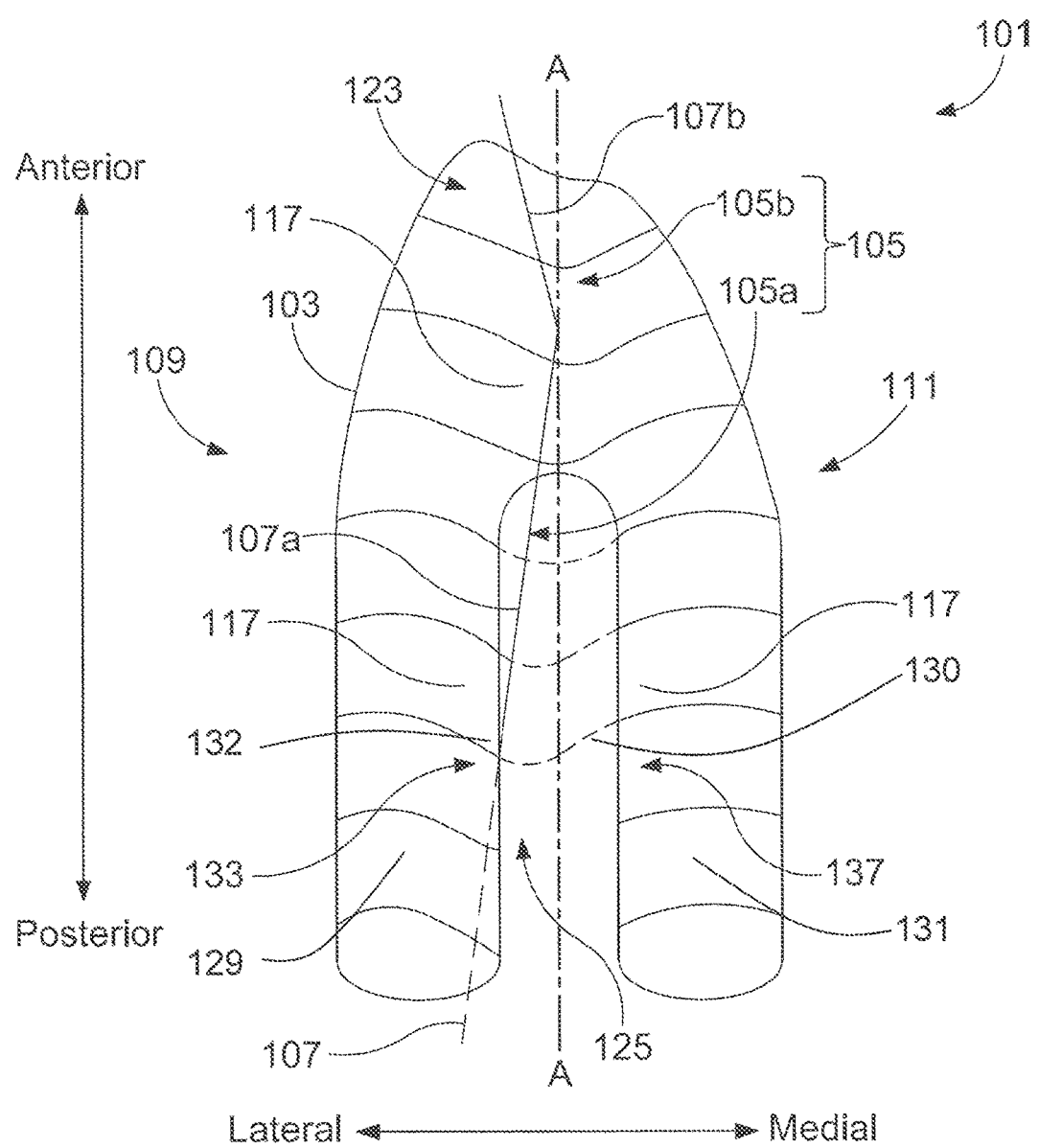
FIG. 2a shows a surface projection of another femoral component for a knee prosthesis.

FIGS. 1a and 2a show a two-dimensional projection of the shape of a femoral component 101 for a knee prosthesis, for example a femoral component for a total knee replacement (TKR). The femoral component 101 is a complex three-dimensional shape and is difficult to accurately represent in two dimensions. In FIGS. 1a and 2a, the outline represents a body portion 103 of the femoral component 101 as projected onto a piece of paper. FIGS. 1a and 2a show a number of contour lines indicating the cross-sectional shape of the body portion 103 at various points along the surface projection. From these contour lines a trochlear groove, commonly referred to as a patella track 105, is shown running anterior-posteriorly around the body portion 103. The direction of the patella track 105 is indicated by line 107.

Whilst FIGS. 1a and 2a show a femoral component configured to be implanted in a patient's right knee, the claimed invention may be adapted to a femoral component configured to be implanted in a patient's left knee.

In FIGS. 1a and 2a, the body portion 103 comprises a lateral portion 109, for example a lateral condyle, and a medial portion 111, for example a medial condyle, when the femoral component 101 is in an implanted configuration. A parasagittal plane is located in between the lateral portion 109 and the medial portion 111, for example at the intersection between the lateral condyle and the medial condyle. In FIGS. 1a and 2a, the three-dimensional parasagittal plane is represented by line A-A, which may be the centreline of the femoral component 101.

Figure 1B:
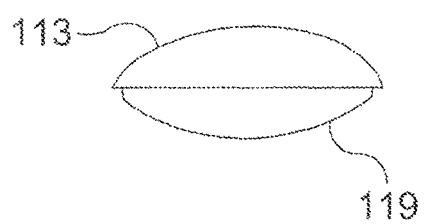
FIG. 1b shows a cross section of a prosthetic patella.
Figure 2B:
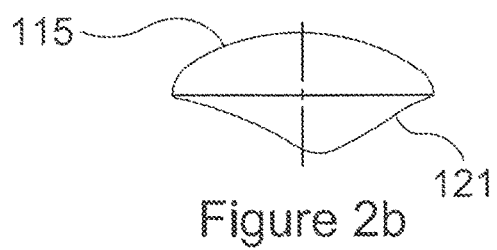
FIG. 2b shows a cross section of a natural patella.

In FIG. 1a, the patella track 105 is configured to guide a prosthetic patella 113, for example a patella button shown in FIG. 1b. In FIG. 2a, the patella track 105 is configured to guide a natural patella 115, shown in FIG. 2b, or an anatomically shaped prosthetic patella button. The patella track 105 comprises an articular surface 117 configured to engage an articular surface 119 of the prosthetic patella 113 or an articular surface 121 of the natural patella 115. The articular surface 119 of the prosthetic patella 113 is domed shaped, whereas the articular surface 121 of the natural patella 115 is asymmetrically curved. It is appreciated, however that the prosthetic patella 113 may be at least partially anatomically shaped. The articular surface 117 of the patella track 105 may therefore be of any appropriate form such that the articular surface 117 of the patella track at least partially conforms to and engages the articular surface 119, 121 of the natural or prosthetic patella 113, 115 respectively. The articular surface 117 of the patella track is configured to guide the patella 113, 115 as the knee prosthesis articulates through a range of motion. For example, the patella track 105 is configured to guide the patella 113, 115 away from an anterior end 123 of the patella track 105 towards a posterior end 125 of the patella track 105 during flexion of the knee. It will be appreciated that due to the u shape of the femoral component the anterior end of the patella track is also the proximal end of the track.

Towards the front of the body portion 103, the lateral portion 109 and the medial portion 111 are joined, and the articular surface 117 of the patella track runs continuously between the lateral portion 109 and the medial portion 111. Towards the rear of the femoral component, the lateral portion 109 and the medial portion 111 separately form the lateral and medial condyles of the femoral component, thereby forming a medial edge portion 133 of the lateral portion 109 and a lateral edge portion 137 of the medial portion 111. The articular surface 117 of the patella track is disposed on the respective edge portions 133, 137 of the lateral and medial condyles such that the patella track 105 runs in between the condyles. In this manner, during flexion of the knee the patella 113, 115 is guided anterior-posteriorly around the body portion 103. The dotted contour lines between the condyles indicate where the articular surface 119, 121 of the patella 113, 115 would lie as the patella 113, 115 tracks along the patella groove 105 in between the condyles.

The patella track 105 comprises a first portion 105a that is directed laterally away from the parasagittal plane as it extends towards the posterior end 125 of the patella track 105. In FIGS. 1a and 2a, line 107a represents the direction of the first patella track portion 105a and indicates how the patella 113, 115 tracks around the femoral component 101. In FIGS. 1a and 2a, the anterior end of line 107a is coincident with the line A-A, indicating that the first patella track portion 105a starts on the parasagittal plane and diverges progressively further laterally from the parasagittal plane as it progresses towards the posterior end 125 of the patella track 105. However, the anterior end of line 107a may be located at any appropriate position, for example laterally or medially of line A-A, such that the first patella track portion 105a starts laterally or medially of the said parasagittal plane, or further forward (anterior) or back (posterior) than shown in the diagrams.

Trochlear grooves vary from person to person, and the location of the patella track in the implant may be tailored to match the trochlear groove of a patient's natural knee if required.

The first patella track portion 105a is configured to guide the patella 113, 115 during articular motion of the knee such that, as the knee articulates from a position where the knee is partially flexed towards a position where the knee is fully flexed, the patella 113, 115 tracks laterally away from the parasagittal plane, i.e. from the centre of the knee joint outwardly in the direction of the lateral edge). In this manner, the femoral component 101 according to the present disclosure improves the patello-femoral kinematics thereby reducing the incidence of adverse events relating to the patello-femoral joint and improper patella 113, 115 tracking during articulation of the knee.

The first patella track portion does not need to extend all the way around the implant to its most posterior/distal end because in use, at maximum flexion, the patella will never reach this point. The precise location of the posterior end of the patella track varies from person to person, but typically is in the region of the last broken contour line 130 (i.e. where line 107 transitions from being solid to broken). The articular surface 117 of the patella track thus only needs to extend this far—up to the predicted most posterior location of the patella, when the implant is in use.

In FIGS. 1a and 2a, the patella track 105 comprises a second portion 105b that is directed laterally away from the parasagittal plane as it extends towards the anterior/proximal end 123 of the patella track 105. The line 107b represents the direction of the second patella track portion 105b and indicates how the patella 113, 115 tracks around the femoral component 101. In FIGS. 1a and 2a, the posterior end of line 107b is coincident with the line A-A, indicating that the second patella track portion 105b starts on the parasagittal plane and diverges progressively further laterally from the parasagittal plane as is extends towards the anterior/proximal end 123 of the patella track 105. However, the posterior end of line 107b may be located at any appropriate position, for example laterally or medially of line A-A, such that the second patella track portion 105b starts laterally or medially of the said parasagittal plane. The posterior end of the line 107b may also be anterior or posterior to the location shown in the diagrams.

The second patella track portion 105b is configured to guide the patella 113, 115 during articular motion of the knee such that, as the knee articulates from a position where the knee is partially flexed towards a position where the knee is fully extended, the patella 113, 115 tracks laterally away from the parasagittal plane.

In the example shown in FIGS. 1a and 2a, the first and second patella track portions 105a, 105b extend continuously into each other, so as to permit the patella 113, 115 to be guided continuously along the patella track 105 during articulation of the knee. For example, in extension, the patella 113, 115 is generally unconstrained and may be guided into the patella track 105 as the knee begins to flex. To facilitate this, the anterior end of the second patella track portion may be shallower than the remainder of the track, such that the implant is flatter in this region. As the track progresses more posteriorly the depth of the track increases. This has the effect that as the knee flexes, the patella is guided into the track and becomes "engaged" with the track.

Once the patella 113, 115 is engaged with the second patella track portion 105b, it will track in a medial direction towards the parasagittal plane as the knees continues to flex. The point where the second patella track portion 105b joins the first patella track portion 105a lies on the parasagittal plane disposed at the intersection between the lateral and medial portions 109, 111. At this point, the centre of the patella, 113, 115 is approximately located on the parasagittal plane of the femoral component 101. As stated above, the join between the first and second patella track portions 105a, 105b need not lie on the parasagittal plane.

In the example of FIGS. 1a and 2a, the join between the second patella track portion 105b and the first patella track portion 105a forms an inflexion point in the line of action 107 of the patella 113, 115. As the knee continues to flex further, the direction in which the patella 113, 115 tracks changes from the medial direction to the lateral direction such that at approximately 90° flexion the centre of the patella 113, 115 is located over the medial edge portion 133 of the lateral condyle.

Figure 4:
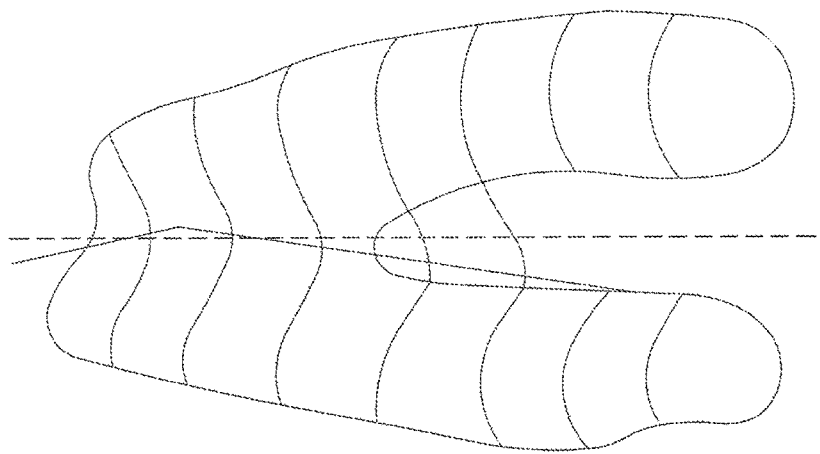
FIG. 4 shows a surface projection of a natural femur.

It will be appreciated that the degree of flexion required for the patella to reach this location varies from person to person. Furthermore, the extent of the lateral tracking may vary from person to person. Thus the location and contours of the patella track in an implant can be adjusted if required, for example to match the kinematics of a patient's natural knee. An example of the contours in a natural knee is shown in FIG. 4.

In another implant, for example, the patella track 105 may comprise one or more connecting portions configured to join the posterior end of the second patella track portion 105b to the anterior end of the first patella track portion 105a. For example, the patella track 105 may comprise a third patella track portion that extends along the line A-A such that the patella 113, 115 tracks in the parasagittal plane while on the third track portion. The connecting portion could be curved, such that the inflexion point between the second and first track portions forms a smooth curve.

In FIGS. 1a and 2a, the line of action 107 of the patella track 105 is represented by straight lines 107a, 107b, which demonstrate a linear relationship between the degree of flexion of the knee and the distance by which the patella 113, 115 tracks away from the parasagittal plane. However, in three dimensions, the line of action 107 of the patella track 105 is curved around the body portion 103 of the femoral component 101. In another example, the projected line of action 107 of the patella track 105 may be curved such that the patella 113, 115 does not track linearly away from the parasagittal plane as the knee flexes. In the examples of FIGS. 1a and 2a, the lines of action 107a, 107b are each angled at approximately 7° to the line A-A, although any other appropriate angle may be employed. In a further example, the shape of the line of action 107 of the patella track 105 may be selected according to the requirements of individual patients.

The femoral component, and in particular the condyles of the femoral component, also include a bearing articular surface, which is configured to articulate in use with a bearing component of a knee prosthesis. Numeral 129 indicates the lateral articular bearing surface, whilst reference numeral 131 indicates the medial bearing articular surface. The articular surface 117 of the patella track overlaps with the articular bearing surfaces 129, 131 on edge regions 133, 137 for a small portion of the first track portion 107a. This overlap region is indicated general by numeral 132. It is desirable for the cross-section of the articular bearing surface 129, 131 to be substantially the same as the cross-section of the patella track articular surface 117 in this overlap region to facilitate the smooth articulation of the joint. The cross-section of the articular bearing surface 129, 131 may be substantially constant.

Figure 3:
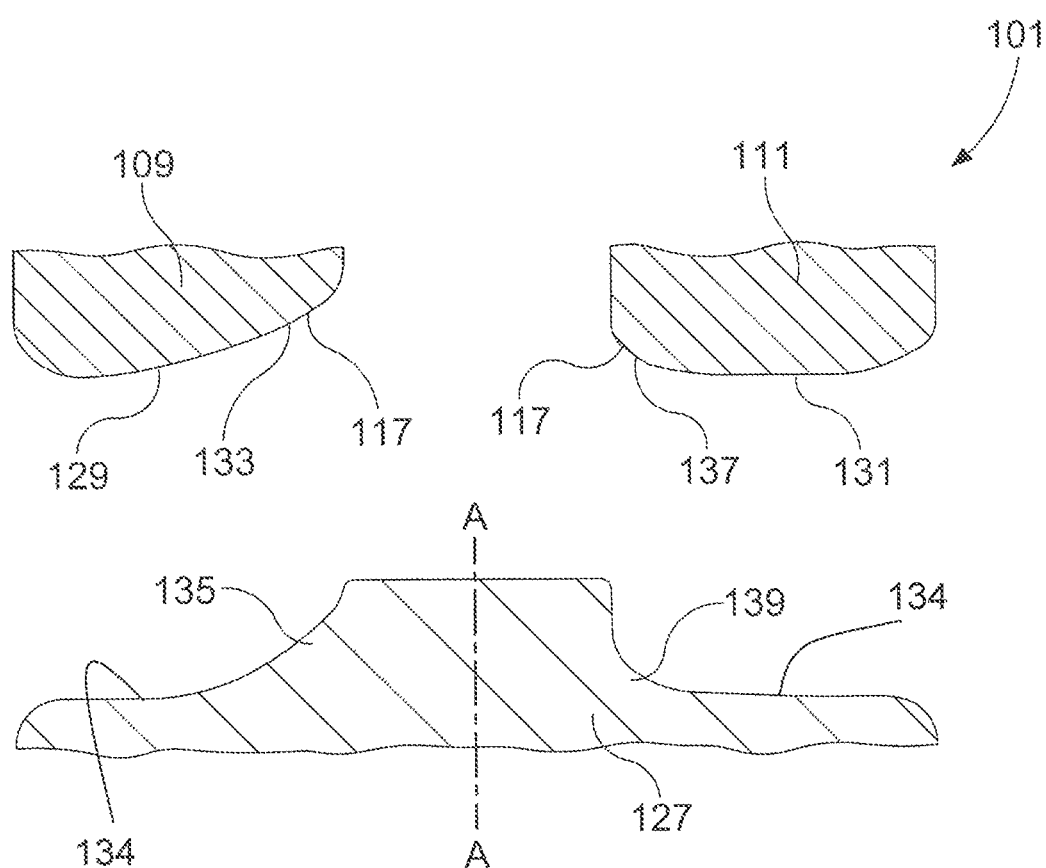
FIG. 3 shows a partial cross section of a femoral component and a bearing component for a knee prosthesis.
Figure 5:
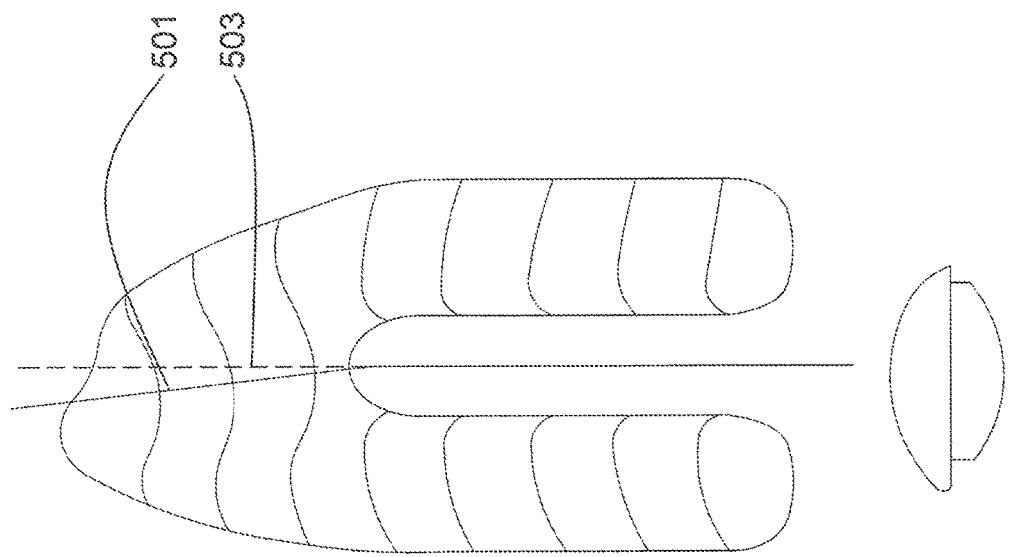
FIG. 5 shows a surface projection of a femoral component of a prior art knee prosthesis and a cross section of a prosthetic patella.

FIG. 3 shows a cross section in the coronal plane through the femoral component 101 and a bearing component 127 of the knee prosthesis. The lateral and medial condyles of the body portion 103 comprise articular bearing surfaces 129, 131 configured to engage femoral bearing surfaces of the bearing component 127. In this manner, the articular bearing surfaces 129, 131 of the femoral component may be optimised for tibio-femoral articulation and the articular surface 117 of the patella track 105 may be optimised for patellofemoral articulation. At least a portion of the articular surface 117 of the patella track 105 may be configured to engage the bearing component 127. Thus all the bearing surfaces of the knee prosthesis as a whole (i.e. the patella track and bearing articular surfaces 117, 129, 131 on the femoral component, the femoral articular surfaces 134 of the bearing component and the articular surface on the patella) should be complementary in shape to facilitate smooth joint articulation.

As shown in FIG. 3, the medial edge portion 133 of the lateral condyle comprises a shallower profile than the lateral edge portion 137 of the medial condyle. The bearing component 127 comprises a lateral corner portion 135 configured to engage the medial edge portion 133 of the lateral condyle, and a medial corner portion 139 configured to engage the lateral edge portion 137 of the lateral condyle. The lateral corner portion 135 may be higher, for example by approximately 2 to 3 mm, than the medial corner portion 139 in an implanted configuration. As a result, the lateral tracking of the patella 113, 115 is enhanced, compared to a bearing component comprising similarly shaped corner portions 135, 139.

As can clearly be seen in FIG. 3, the coronal cross-section of the tibial component is asymmetric about the parasagittal plane (denoted by the line A-A). In particular, the lateral corner portion 135 is more oblique than the medial corner portion 139. This helps to ensure that the shape of the tibial bearing surface in the coronal plane matches the distal articular surface of the femoral component in the coronal plane. This improves the interaction between the tibial and femoral components when the femur is in extension.

It will be appreciated by those skilled in the art that although the disclosure has been described by way of example with reference to one or more examples, it is not limited to the disclosed examples and that alternative examples could be constructed without departing from the scope of the invention as defined by the appended claims.

For instance, although the invention has been described primarily with respect to total knee replacements, it will be appreciated that the same principles can be incorporated into partial knee replacements, both unicompartmental (patellofemoral joint, medial or lateral condyles) and bi-compartmental.

In the case of a lateral unicondylar knee replacement for instance, the posterior portion of the patella track would be arranged to direct the patella laterally relative to the medial edge of the component (which is in use implanted toward the centre of the knee joint). Conversely, in the case of a medial unicondylar knee replacement the posterior portion of the patella track would be arranged to direct the patella laterally relative the lateral edge of the component (which is in use implanted toward the centre of the knee joint). In either case, the aim is to provide a patella track having articular surfaces which, when combined with the remaining unresected articular surfaces of the joint, mimic the natural structure of the trochlear groove more closely than existing knee replacement components.

The invention claimed is:

1. A femoral component for a knee prosthesis, the femoral component comprising:
   a body portion having:
      a lateral portion and a medial portion when in an implanted configuration; and
      a patella track extending anterior-posteriorly around the body portion;
   wherein the patella track comprises a first patella track portion that is directed laterally as it progresses towards a posterior end of the patella track and a second patella track portion that is directed laterally as it extends towards an anterior/proximal end of the patella track, the first patella track portion and the second patella track portion extending continuously into each other such that an inflexion portion is created in the patella track at a junction between the first and second patella track portions;
   wherein a patella that is engaged in the patella track is caused to change direction by the inflexion portion.

2. A femoral component according to claim 1, wherein a parasagittal plane is located at an intersection between the lateral portion and the medial portion, and wherein the first patella track portion starts at a point on or near the parasagittal plane and diverges progressively further laterally away from its starting point as it extends towards the posterior end of the patella track.

3. A femoral component according to claim 1, wherein the first patella track portion is configured to guide the motion of a natural patella or a prosthetic patella during articular motion of the knee such that as the knee articulates from a position where the knee is partially flexed towards a position where the knee is fully flexed the natural patella or the prosthetic patella tracks laterally.

4. A femoral component according to claim 1, wherein a parasagittal plane is located at an intersection between the lateral portion and the medial portion, and wherein the second patella track portion starts at a point on or near the parasagittal plane and diverges progressively further laterally from its starting point as it extends towards the anterior/proximal end of the patella track.

5. A femoral component according to claim 1, wherein the second patella track portion is configured guide the motion of a natural patella or a prosthetic patella during articular motion of the knee such that as the knee articulates from a position where the knee is partially flexed towards a position where the knee is fully extended the natural patella or the prosthetic patella tracks laterally.

6. A femoral component according to claim 1, wherein the patella track comprises a groove having a depth, and wherein the depth of the groove is shallower at the anterior/proximal end of the second patella track portion than it is at a posterior end of the second patella track portion.

7. A femoral component according to claim 1, wherein a medial edge portion of the lateral portion and a lateral edge portion of the medial portion at least partially form the lateral and medial edge portions of the patella track respectively.

8. A femoral component according to claim 1, wherein the patella track comprises an articular surface configured to engage a natural patella or a prosthetic patella.

9. A femoral component according to claim 8, wherein the articular surface of the patella track is configured to at least partially conform to an articular surface of the natural patella or the prosthetic patella.

10. A femoral component according to claim 1, wherein the component comprises a bearing articular surface configured to engage a bearing component having a tibial articular surface.

11. A femoral component according to claim 10, wherein an overlap region of the articular surface of the patella track is further configured to engage the bearing component.

12. A femoral component according to claim 10, wherein a cross section of the posterior end of the patella track is substantially the same as a cross section of a tibial articular surface such that the bearing articular surface blends smoothly into the articular surface of the patella track.

13. A femoral component according to claim 1, wherein the lateral portion comprises a lateral condyle and the medial portion comprises a medial condyle.

14. A kit of parts for a knee prosthesis including:
   the femoral component of claim 1;
   a tibial component; and,
   a patella button.

15. The kit of claim 14, wherein a bearing surface of the tibial component has a shape which is complementary to a bearing articular surface of the femoral component, and wherein an articular surface of the patella track of the femoral component has a complementary shape to an articular surface of the patella button.

16. The femoral component according to claim 1, wherein the inflexion portion is located closer to the anterior/proximal end of the patella track, such that a patella engaged in the track is caused to change direction prior to the knee reaching 90 degrees of flexion.

17. The femoral component according to claim 1, wherein the inflexion portion is located anterior to an intercondylar notch.

\* \* \* \* \*